United States Patent [19]

Tatee et al.

[11] Patent Number: 4,954,642
[45] Date of Patent: Sep. 4, 1990

[54] FORSKOLIN COMPOUNDS

[75] Inventors: Tochiro Tatee, Tokyo; Takashi Takahira, Yono; Kouwa Yamashita, Urawa; Masao Sakurai, Ageo; Akira Shiozawa, Omiya; Kazuhisa Narita, Tokyo, all of Japan

[73] Assignee: Nippon Kayaku Kabushiki Kaisha, Tokyo, Japan

[21] Appl. No.: 361,763

[22] Filed: May 30, 1989

Related U.S. Application Data

[63] Continuation-in-part of Ser. No. 926,102, Nov. 3, 1986, abandoned.

[30] Foreign Application Priority Data

Nov. 15, 1985 [JP] Japan ................................ 60-254693
Jan. 27, 1986 [JP] Japan ................................ 61-13771
Mar. 13, 1986 [JP] Japan ................................ 61-53709
Mar. 26, 1986 [JP] Japan ................................ 61-65947

[51] Int. Cl.$^5$ .......................................... C07D 311/92
[52] U.S. Cl. .................................................. 549/389
[58] Field of Search .......................... 549/389; 514/455

[56] References Cited

U.S. PATENT DOCUMENTS 4,088,659   5/1978   Bhat ........................................ 549/389
4,134,986   1/1979   Bajwa et al. ........................... 514/455
4,639,443   1/1987   Kosley, Jr. et al. ................. 514/228.2
4,639,446   1/1987   Kosley, Jr. et al. ................. 514/228.2

FOREIGN PATENT DOCUMENTS 0116713   8/1984   European Pat. Off. ............. 514/455
0193132   3/1985   European Pat. Off. .......... 514/228.2
0191166   8/1986   European Pat. Off. .......... 514/228.2
0217372  10/1986   European Pat. Off. ............. 514/455
0252482   7/1987   European Pat. Off. ............. 514/455
0217370   3/1988   European Pat. Off. ............. 514/455
0268256   5/1988   European Pat. Off. ............. 514/455
3535086   4/1987   Fed. Rep. of Germany ...... 514/455
176585  11/1985   Japan ................................. 514/228.2
210081   1/1986   Japan ................................. 514/228.2
WO85/03637   8/1985   PCT Int'l Appl. ............. 514/228.2
WO88/05047   7/1988   PCT Int'l Appl. ................. 514/455

OTHER PUBLICATIONS

Metzger et al, "The Positive Inotropic-Acting Forskolin, a Potent Adenylatecyclase Activator", Arzneimittel-Forschung, vol. 31, pp. 1248–1250, (1981).
Bhat *Journal of Medicinal Chemistry*, "The Antihypertensive and Positive Inotropic Diterpene Forskolin: Effects of Structural Modifications on Its Activity" vol. 26, pp. 486–492, (1983).

*Primary Examiner*—Mary C. Lee
*Assistant Examiner*—Zinna Northington-Davis
*Attorney, Agent, or Firm*—Banner, Birch, McKie & Beckett

[57] ABSTRACT

This invention relates to forskolin derivatives, their physiologically acceptable salts, and a process for producing these compounds. The forskolin derivative is represented by the general formula

[chemical structure: decalin-based forskolin skeleton with substituents $R^1O$, $R^4$, $OH$, $OR^2$, $OR^3$, and a ketone]

wherein;
I. when $R^1$ is hydrogen and $R^4$ is vinyl, ethyl, or cyclopropyl,
  (1) either of $R^2$ and $R^3$ denotes a residue represented by the formula $$CO(CH_2)_m N\begin{matrix}R^5\\R^6\end{matrix},$$

wherein each of $R^5$ and $R^6$ denotes hydrogen or lower alkyl or $R^5$ and $R^6$ combine with each other to form a lower alkylene chain which may or may not contain an oxygen or nitrogen atom and m is an integer of 1 to 5, and the other one of $R^2$ and $R^3$ denotes hydrogen or a residue represented by the formula $CO(CH_2)_n X$, X being hydrogen or $$-N\begin{matrix}R^7\\R^8\end{matrix}$$

wherein, each of $R^7$ and $R^8$ denotes hydrogen or lower alkyl or $R^7$ and $R^8$ combine with each other to form a lower alkylene chain which may or may not contain an oxygen or nitrogen atom, and n being an integer of 1 to 5, or
  (2) $R^2$ denotes hydrogen or —COCH$_2$CH$_2$CO$_2$H and $R^3$ denotes hydrogen, —COCH$_3$, —COCH$_2$CH$_2$CH$_2$CO$_2$H, or —COCH(OH)CH$_2$OH with the proviso that $R^3$ is one of the last two residues when $R^2$ is hydrogen, and
II. when
$R^1$ is a residue represented by a formula of CO(CH$_2$)$_p$CO$_2$H and $$CO(CH_2)_q N\begin{matrix}R^9\\R^{10}\end{matrix}$$

wherein, each of $R^9$ and $R^{10}$ denotes hydrogen or lower alkyl, p is an integer of 0 to 5, and q is an integer of 1 to 5,
$R^2$ denotes hydrogen, $R^3$ denotes acetyl, and $R^4$ denotes vinyl.

8 Claims, No Drawings

FORSKOLIN COMPOUNDS

This application is a continuation-in-part of application Ser. No. 06/926,102, filed Nov. 3, 1986, now abandoned.

BACKGROUND OF THE INVENTION

1. Field of the Invention

The present invention relates to a novel forskolin derivative having positive inotropic, hypotensive, and adenylate cyclase-stimulating actions.

2. Description of the Prior Art

There is already known forskolin that has positive inotropic, hypotensive, and adenylate cyclase-stimulating actions [Japanese Patent Application Kokai (Laid-Open) No. 79015/77 and Arzneim.-Forsch., 31, 1248 (1981)].

However, forskolin is water-soluble as scarcely as in a concentration of 0.0026% at room temperature and therefore special pharmaceutical device is necessary in order to administer it. Thus it has been desired to develop a water-soluble derivative of forskolin.

SUMMARY OF THE INVENTION

Under the circumstances, the present inventors made extensive studies, and as a result have found that the following forskolin derivatives and their physiologically acceptable salts are more soluble than folskolin in acidic or neutral or basic solution and have positive inotropic, hypotensive, and adenylate cyclase-stimulating actions. That is forskolin derivatives represented by the general formula

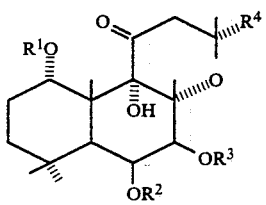

(I)

wherein;

I. when $R^1$ is hydrogen and $R^4$ is vinyl, ethyl, or cyclopropyl, (1) either of $R^2$ and $R^3$ denotes a residue represented by the formula

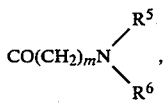

wherein each of $R^5$ and $R^6$ denotes hydrogen or lower alkyl or $R^5$ and $R^6$ combine with each other to form a lower alkylene chain which may or may not contain an oxygen or nitrogen atom and m is an integer of 1 to 5, and the other one of $R^2$ and $R^3$ denotes hydrogen or a residue represented by the formula $CO(CH_2)_nX$, X being hydrogen or

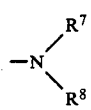

wherein, each of $R^7$ and $R^8$ denotes hydrogen or lower alkyl or $R^7$ and $R^8$ combine with each other to form a lower alkylene chain which may or may not contain an oxygen or nitrogen atom, and n being an integer of 1 to 5, or (2) $R^2$ denotes hydrogen or $-COCH_2CH_2CO_2H$ and $R^3$ denotes hydrogen, $-COCH_3$, $-COCH_2CH_2CH_2CO_2H$, or $-COCH(OH)CH_2OH$ with the proviso that $R^3$ is one of the last two residues when $R^2$ is hydrogen, and II. when $R^1$ is a residue represented by a formula of $CO(CH_2)_pCO_2H$ and

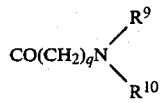

wherein, each of $R^9$ and $R^{10}$ denotes hydrogen or lower alkyl, p is an integer of 0 to 5, and q is an integer of 1 to 5, $R^2$ denote hydrogen, $R^3$ denotes acetyl, and $R^4$ denotes vinyl.

Based on the above finding, the present invention has been accomplished.

DETAILED DESCRIPTION OF THE INVENTION

In the above general formula (I), the lower alkyl group is, for example, an alkyl of 1 to 4 carbon atoms such as methyl, ethyl, propyl, or butyl. The lower alkylene chain which may or may not contain an oxygen or nitrogen atom is, for example, a $C_3$—$C_5$ chain such as $-(CH_2)_3-$, $-(CH_2)_5-$, $$-(CH_2)_{\overline{x}}N(H)(CH_2)_{\overline{y}}-,$$

or $-(CH_2)_{2}-O-(CH_2)_{2}-$.

The residue

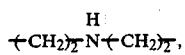

which either of $R^2$ and $R^3$ in formula (I) denotes is, for example, dimethylaminoacetyl, diethylaminoacethyl, diethylaminopropionyl, butylaminoacetyl, dimethylaminopropionyl, dimethylaminobutyryl, pyrrolidinobutyryl, pyrrolidinoacetyl, piperazinoacetyl, or morpholinoacetyl group. The residue $-CO(CH_2)_nX$ which the other one of $R^2$ and $R^3$ denotes is, for example, acetyl, propionyl, butyryl, or any of the above-cited various aminoacyl groups. Preferred examples of the compound represented by formula (I) have a lower alkylcarbonyl group, e.g. acetyl as $R^3$ and

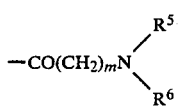

as $R^2$, wherein m is 1 to 4 and $R^5$ and $R^6$ are lower alkyl groups.

Now, description is given on the process for producing compounds represented by formula (I).

1. Compounds represented by formula (I) in which both $R^1$ and $R^2$ are hydrogen atoms and $R^3$ is

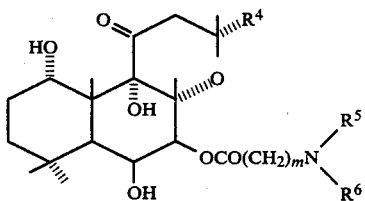 (X)

that is, compounds of the formula

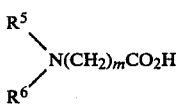 (II)

can be produced each according to some of the following processes:

(1) 7-Deacetylforskolin ($R^1=R^2=R^3=H$, $R^4=-CH=CH_2$), or 7-deacetyl-14,15-dihydroforskolin ($R^1=R^2=R^3=H$, $R^4=CH_2CH_3$) or 13-cyclopropyl-7-deacetyl-14,15-dinorforskolin ($R^1=R^2=R^3=H$, $R^4=$cyclopropyl) is condensed with a compound represented by the general formula

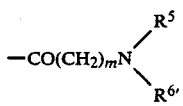

(wherein $R^5$, $R^6$ and m are as defined above) or with a reactive derivative thereof.

(2) 7-Deacetylforskolin or 7-deacetyl-14,15-dihydroforskolin or 13-cyclopropyl-7-deacetyl-14,15-dinorforskolin is condensed with a compound represented by the formula Y—(CH$_2$)$_m$COOH (III)

(wherein Y denotes halogen or an alkyl- or arylsulfonyloxy group and m is as defined above) or with a reactive derivative thereof, and the condensate is reacted with a compound represented by the general formula

 (IV)

(wherein $R^5$ and $R^6$ are as defined above).

(3) 7-Deacetylforskolin or 7-deacetyl-14,15-dihydroforskolin or 13-cyclopropyl-7-deacetyl-14,15dinorforskolin is condensed with a compound represented by the general formula CH=CH$_2$—(CH$_2$)$_{m'-2}$COOH (V)

(wherein m' is an integer of 2 to 4) or with a reactive derivative thereof, and the condensate is reacted with a compound represented by the above general formula (IV).

When carboxylic acids of general formulas (II), (III), and (V) are used as such in the above condensations (1), (2), and (3) respectively, desirable results are obtained by carrying out the condensation in a solvent such as benzene, chloroform, ether, or ethyl acetate in the presence of dicyclohexylcarbodiimide, dicyclohexylcarbodiimide +4-dimethylaminopyridine, carbonyldiimidazole, or diphenylphosphorylazide for a period of 0.5 to 72 hours, preferably, 2 to 48 hours at a temperature of e.g. from −20° to +200° C., usually from a temperature under cooling with ice to about the boiling point of the used solvent.

Herein, the compounds of general formula (II) include, for example, dimethylaminoacetic acid, butylaminoacetic acid, diethylaminoacetic acid, pyrrolidinoacetic acid, piperazinoacetic acid, morpholinoacetic acid, dimethylaminopropionic acid, and pyrrolidinobutyric acid.

The compounds of general formula (III) include, for example, haloacetic acids (e.g. chloroacetic acid and bromoacetic acid), chloropropionic acid, chlorobutyric acid, chlorovaleric acid, methanesulfonyloxyacetic acid, p-toluenesulfonyloxybutyric acid, and methanesulfonyloxyvaleric acid.

The compounds of general formula (V) include, for example, acrylic acid, methacrylic acid, vinylacetic acid, and allylacetic acid.

When compounds of general formulas (II), (III), and (V) are used in the form of reactive derivative in the above condensations (1), (2), and (3), respectively, desirable results are obtained by carrying out the reaction in a solvent such as benzene, chloroform, ether, or ethyl acetate in the presence of a base such as pyridine or triethylamine for a period of 0.5 to 72 hours, preferably, 2 to 48 hours under cooling with ice or at a higher temperature up to about the boiling point of the used solvent.

Reactive derivatives suitable for these condensations include, for example, acid halides, acid anhydrides, mixed acid anhydrides, and Leuches anhydrides.

In the above processes (2) and (3), the reaction with the amine of general formula (IV) is accomplished in a solvent such as dichloromethane with stirring for a period of 0.5 to 5 hours under cooling with ice.

The amine of general formula (IV) is exemplified by dimethylamine, butylamine, diethylamine, pyrrolidine, piperazine, and morpholine.

(4) Compound No. 26, shown in Table 1 later, is used for this condensation, the reaction is conducted in a solvent such as benzene, chloroform, ether, or ethyl acetate in the presence of a base such as pyridine or triethylamine. Favorable results are obtainable also by carrying out the reaction for a period of 2 to 48 hours under cooling with ice or at a higher temperature up to about the boiling point of the used solvent.

(5) Compound No. 27 is obtained by condensation of 7-deacetylforskolin with glyceric acid or a reactive derivative thereof. When glyceric acid is used as such for condensation, desirable results are obtained by carrying out the reaction in a solvent such as benzene, chloroform, ether, or ethyl acetate in the presence of dicylohexylcarbodiimide, dicyclohexylcarbodiimide+4-dimethylaminopyridine, carbonyldiimidazole, or diphenylphosphorylazide for a period of 2 to 48 hours under cooling with ice or at a higher temperature up to about the boiling point of the used solvent.

When a reactive derivative of glyceric acid is used for this condensation, the reaction is conducted in a solvent such as benzene, chloroform, ether, or ethyl acetate in the presence of a base such as pyridine or triethylamine. Favorable results are obtainable also by carrying out the reaction for a period of 2 to 48 hours under cooling with ice or at a higher temperature up to about the boiling point of the used solvent.

The reactive derivative is exemplified by acid halides, acid anhydrides, mixed acid anhydrides, and Leuchs anhydrides.

2. The compound of formula (I) in which both $R^1$ and $R^3$ are hydrogen atoms and $R^2$ is other than hydrogen, that is, the compound of the formula

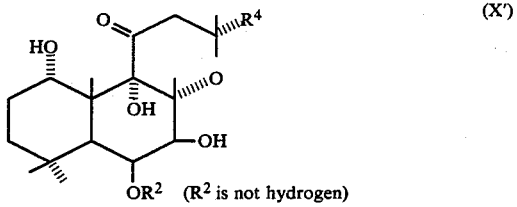

(X')

$OR^2$ ($R^2$ is not hydrogen)

can be produced by dislocating the 7-positioned substituent of 7-substituted forskolin or 7-substituted-14,15-dihydroforskolin or of 7-substituted-13-cyclopropyl-14,15-dinorforskolin obtained by the above process 1, to the 6-position.

This rearrangement is accomplished by reacting said 7-substituted compound with 0.1 to 10 equivalents, preferably 1 to 3 equivalents, of an inorganic base used as an alkali metal hydride, hydroxide, or carbonate (e.g. NaOH, KOH, $K_2CO_3$, or NaH) or of an organic base such as a tri(lower alkyl)amine (e.g. triethylamine) or 1,8-diazabicyclo[5,4,0]-7-undecene in an organic solvent such as dimethylsulfoxide, N,N-dimethylformamide, methanol, acetone, acetonitrile, dioxane or tetrahydrofuran or a mixture of water with each of these solvents, preferably a mixture of water with N,N-dimethylformamide or acetonitrile. The reaction is conducted for a period of 1 minute to 48 hours at a temperature of ca. $-20°$ to ca. $+200°$ C., normally from a temperature under cooling with ice to about the boiling point of the used solvent, preferably for a period of 30 minutes to 1 hour at room temperature.

The compound of formula (X') can also be produced by treating the intermediate resulting from the condensation step of 1-(2) or 1-(3) above, in the same manner as in process 2 above, followed by reaction with an amine of the above formula (IV).

3. The compound of formula (I) in which $R^2$ is $-COCH_2CH_2COOH$ and both $R^1$ and $R^3$ are hydrogen atoms, that is, the compound of the formula

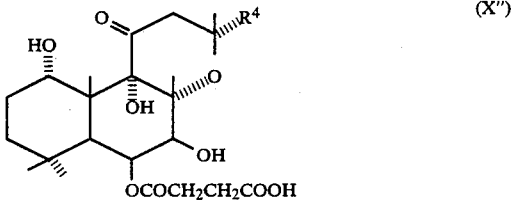

(X'')

$OCOCH_2CH_2COOH$ can be produced in the following way: Forskolin having the substituent $-OCOCH_2CH_2COOH$ at the 7-position is prepared according to the procedure of 1-(4) above but using succinic anhydride in place of glutaric anhydride, and the 7-positioned substituent is dislocated to the 6-position.

This rearrangement is accomplished by reacting said 7-substituted forskolin with 0.1 to 10 equivalents, preferably 1 to 3 equivalents, of an inorganic base such as NaOH, KOH, $K_2CO_3$, or NaH or of an organic base such as triethylamine or 1,8-diazabicyclo[5,4,0]-7-undecene in a polar solvent such as dimethylsulfoxide, N,N-dimethylformamide, methanol, acetone, or acetonitrile, dioxane or tetrahydrofuran or a mixture of water with each of these solvents, preferably a mixture of water with N,N-dimethylformamide or acetonitrile. The reaction is conducted for a period of minute to 48 hours under cooling with ice or at a higher temperature up to about the boiling point of the used solvent, preferably for a period of 30 minutes to 1 hour at room temperature.

4. Compounds represented by formula (I) in which $R^1$ is hydrogen and both $R^2$ and $R^3$ are other than hydrogen, that is, compounds of the formula

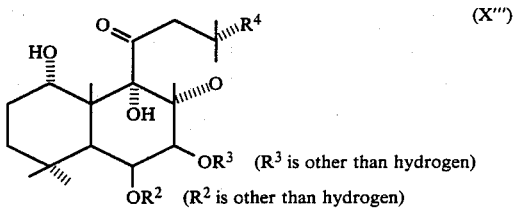

(X''')

$OR^3$ ($R^3$ is other than hydrogen)
$OR^2$ ($R^2$ is other than hydrogen)

can be produced each according to some of the following processes:

(1) 6-Substituted 7-deacetylforskolin or 6-substituted 7-deacetyl-14,15-dihydroforskolin or 6-substituted 13-cyclopropyl-7-deacetyl-14,15-dinorforskolin obtained according to the above process 2 or a 6-alkanoyl-7-acetylforskolin obtained in the same manner as described above is condensed with a compound represented by the general formula $Y-(CH_2)_m-COOH$   (VI)

wherein Y and m are the same as in the above formula (III) or with a reactive derivative thereof in the same manner as in 1-(1) above.

The compound of general formula (VI) is exemplified by acetic acid, propionic acid, butyric acid, and acids cited above as compounds of general formula (II).

(2) When the compound to be produced has a nitrogen-containing substituent at the 7-position, this compound can be obtained by carrying out reactions similar to those of 1-(2) or 1-(3) above using any of 6-substituted 7-deacetylforskolin, 6-substituted 7-deacetyl-14,15-dihydroforskolin, -substituted 7-deacetyl-13-cyclopropyl-14,15-dinorforskolin, and 6-alkanoyl-7-deacetylforskolin that are prepared according to the above process 2.

(3) The compound of formula (I) wherein $R^1$ is hydrogen, $R^2$ is $-COCH_2CH_2COOH$, and $R^3$ is $-COCH_3$, $-COCH_2CH_2CH_2COOH$, or $-COCH(OH)CH_2OH$ can be produced by preparing first 6-(2-carboxyethylcarbonyl)-7-deacetylforskolin according to the above process 3, and reacting it secondly with acetic acid or a reactive derivative thereof or acylating it according to the above process 1-(4) or 1-(5).

It may be noted that in the above processes 1 to 4 the 1-positioned hydroxyl group of the starting material 7-deacetylforskolin or its derivative is protected with an acyl group (e.g. acetyl), ether group (e.g. methoxy), or silylether (e.g. t-butyldimethylsilyl), the reaction is carried out by using the resulting protected compound, and the protecting group is removed in the last step, whereby the present inventive compound of formula (I) can also be 5. The compound of formula (I) wherein $R^4$ is ethyl or cylopropyl, that is, 6- and/or 7-di(or mono)-substituted 13-ethyl(or cyclopropyl)-14,15-dinorforskolin can be produced by either hydrogenating 6- and/or 7-di(or mono) substituted forskolin prepared according to the above process 1, 2, or 3 or reacting it with diazomethane in the presence of such a catalyst as palladium acetate.

6. The compound of formula (I) wherein $R^1$ is —$CO(CH_2)_pCOOH$ or

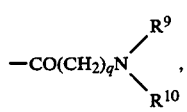

that is, the compound of the formula

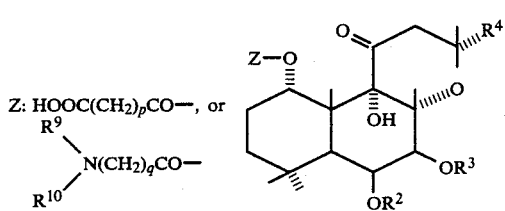

Z: $HOOC(CH_2)_pCO$—, or
$R^9\diagdown$
$\phantom{R^9}N(CH_2)_qCO$—
$R^{10}\diagup$ (wherein $R^2$, $R^3$, $R^4$, $R^9$, $R^{10}$, p and q are as defined above) can be produced by reacting the compound of the formula

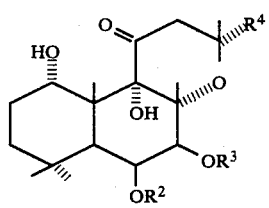

(wherein $R^2$, $R^3$ and $R^4$ are as defined above) with a carboxylic acid represented by the general formula

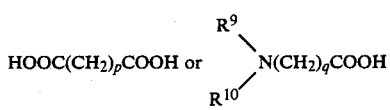

(wherein $R^9$, $R^{10}$, p, and q are as defined above) or with its reactive derivative in a solvent at a temperature of from $-20°$ to $+200°$ C.

7. 6-Aminoalkylcarbonylforskolin or 6-aminoalkylcarbonyl-14,15-dihydroforskolin or 13-cyclopropyl-6-aminoalkylcarbonyl-14,15-dinorforskolin represented by the general formula

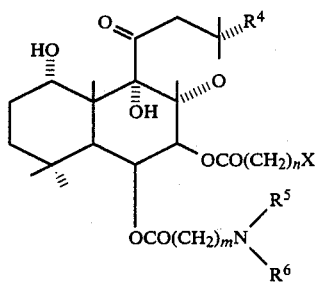

(wherein $R^4$, $R^5$, $R^6$, m, n, and X are as defined above) can be produced by reacting 6-aminoalkylcarbonyl-7-deacetylforskolin or 6-aminoalkylcarbonyl-7-deacetyl-14,15-dihydroforskolin or 13-cyclopropyl-6-aminoalkylcarbonyl-7-deacetyl-14,15-dinorforskolin represented by the general formula

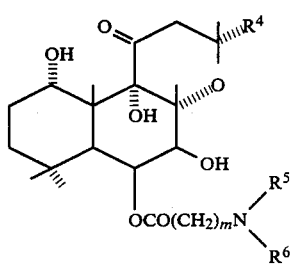

(wherein $R^4$, $R^5$, $R^6$, and m are as defined above) with a carboxylic acid represented by the general formula $HOOC(CH_2)_nX$      (IX)

(wherein X and n are as defined above) or with its reactive derivative in an organic solvent such as dichloromethane, 1,2-dichloroethane, chloroform and diethyl ether or a mixture thereof with water at a temperature, e.g. between ca. $-20°$ and $+200°$ C., preferably between $-5°$ and the boiling point of the used solvent.

6-Aminoalkylcarbonyl-7-deacetylforskolin or 6-aminoalkylcarbonyl-7-deacetyl-14,15-dihydroforskolin or 13-cyclopropyl-6-aminoalkylcarbonyl-7-deacetyl-14,15-dinorforskolin, that is, a starting material represented by general formula (VIII) can be prepared by reacting a base with 7-aminoalkylcarbonyl-7-deacetylforskolin or 13-cyclopropylaminoalkylcarbonyl-7-deacetyl-14,15-dinorforskolin, which is represented by the general formula

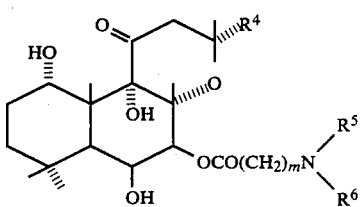

(wherein $R^4$, $R^5$, $R^6$, and m are as defined above) in a polar solvent to dislocate the residue

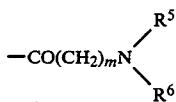

to the 6-position.

It may be noted that in the above processes 1 to 6, the present inventive compound of formula (I) can also be obtained by using compound with carboxyl, hydroxyl, or amino group on $R^1$, $R^2$, or $R^3$ protected with an acyl group (e.g. acetyl), ester group (e.g. methyl ester, ethyl ester), ether group (e.g. methoxy, acetonide), or silyl ether group (e.g. t-butyldimethylsilylether) as intermediate, and the protecting group is removed in the last step.

Unless otherwise noted, any of the above reactions is carried out desirably in an organic solvent such as dichloromethane, 1,2-dichloroethane and chloroform or a mixture thereof with water.

From the reaction product solution, the compound of the present invention is isolated and purified in usual ways, thereby being obtained in the form of free base, free acid, or salt depending upon reaction conditions and the way of after-treatment.

If desired, the free base and the free acid can be transformed each into a salt in the normal may. The free base may be transformed into an inorganic acid addition salt such as hydrochloride, hydrobromide, sulfate, or phosphate or into an organic acid addition salt such as a salt of formic acid, acetic acid, fumaric acid, maleic acid, citric acid, tartaric acid, lactic acid, or methanesulfonic acid.

The free acid may be transformed into a metal salt such as sodium salt, potassium salt, magnesium salt, or calcium salt or into a salt of organic base such as quaternary ammonium salt or pyridinium salt.

Theoretically, there exist optical isomers of the present inventive compounds which have an asymmetric carbon atom in $R^2$ or $R^3$. Therefore these optical isomers are included in the scope of the present invention. The optical isomers can be separated by a known method, e.g. chromatography or fractional crystallization.

Table 1 shows examples of the present inventive compounds produced by the above described process.

TABLE 1

| No. | $R^1$ | $R^2$ | $R^3$ | $R^4$ |
|---|---|---|---|---|
| 1 | H | H | COCH$_2$N(CH$_3$)$_2$ | CH=CH$_2$ |
| 2 | H | H | COCH$_2$NH(CH$_2$)$_3$CH$_3$ | CH=CH$_2$ |
| 3 | H | H | COCH$_2$N(CH$_2$CH$_3$)$_2$ | CH=CH$_2$ |
| 4 | H | H | COCH$_2$N(pyrrolidinyl) | CH=CH$_2$ |
| 5 | H | H | COCH$_2$N(piperazinyl)NH | CH=CH$_2$ |
| 6 | H | H | COCH$_2$N(morpholinyl)O | CH=CH$_2$ |
| 7 | H | H | CO(CH$_2$)$_2$N(CH$_3$)$_2$ | CH=CH$_2$ |
| 8 | H | H | CO(CH$_2$)$_3$N(pyrrolidinyl) | CH=CH$_2$ |
| 9 | H | COCH$_2$N(CH$_3$)$_2$ | H | CH=CH$_2$ |
| 10 | H | COCH$_2$N(CH$_3$)$_2$ | COCH$_3$ | CH=CH$_2$ |
| 11 | H | COCH$_2$N(CH$_3$)$_2$ | COCH$_2$CH$_3$ | CH=CH$_2$ |
| 12 | H | COCH$_2$N(CH$_3$)$_2$ | CO(CH$_2$)$_2$CH$_3$ | CH=CH$_2$ |
| 13 | H | COCH$_2$N(CH$_3$)$_2$ | COCH$_2$N(CH$_3$)$_2$ | CH=CH$_2$ |
| 14 | H | COCH$_2$N(CH$_2$CH$_3$)$_2$ | H | CH=CH$_2$ |
| 15 | H | COCH$_2$N(CH$_2$CH$_3$)$_2$ | COCH$_3$ | CH=CH$_2$ |
| 16 | H | COCH$_2$NH(CH$_2$)$_3$CH$_3$ | H | CH=CH$_2$ |
| 17 | H | CO(CH$_2$)$_2$N(CH$_3$)$_2$ | COCH$_3$ | CH=CH$_2$ |
| 18 | H | CO(CH$_2$)$_2$N(CH$_2$CH$_3$)$_2$ | COCH$_3$ | CH=CH$_2$ |
| 19 | H | CO(CH$_2$)$_3$N(CH$_3$)$_2$ | H | CH=CH$_2$ |

TABLE 1-continued

| No. | R¹ | R² | R³ | R⁴ |
|---|---|---|---|---|
| 20 | H | $CO(CH_2)_3N(CH_3)_2$ | $COCH_3$ | $CH=CH_2$ |
| 21 | H | $COCH_3$ | $COCH_2N(CH_3)_2$ | $CH=CH_2$ |
| 22 | H | $COCH_3$ | $CO(CH_2)_3N\text{(piperidine)}$ | $CH=CH_2$ |
| 23 | H | $CO(CH_2)_2N(CH_3)_2$ | H | $CH=CH_2$ |
| 24 | H | $CO(CH_2)_2N(CH_2CH_3)_2$ | H | $CH=CH_2$ |
| 25 | H | H | $CO(CH_2)_2N(CH_2CH_3)_2$ | $CH=CH_2$ |
| 26 | H | H | $CO(CH_2)_3CO_2H$ | $CH=CH_2$ |
| 27 | H | H | $COCH(OH)CH_2OH$ | $CH=CH_2$ |
| 28 | H | $CO(CH_2)_2CO_2H$ | H | $CH=CH_2$ |
| 29 | H | $CO(CH_2)_2CO_2H$ | $COCH_3$ | $CH=CH_2$ |
| 30 | $COCO_2H$ | H | $COCH_3$ | $CH=CH_2$ |
| 31 | $CO(CH_2)_2CO_2H$ | H | $COCH_3$ | $CH=CH_2$ |
| 32 | $CO(CH_2)_3CO_2H$ | H | $COCH_3$ | $CH=CH_2$ |
| 33 | $CO(CH_2)_4CO_2H$ | H | $COCH_3$ | $CH=CH_2$ |
| 34 | $COCH_2NH_2$ | H | $COCH_3$ | $CH=CH_2$ |
| 35 | $CO(CH_2)_3NH_2$ | H | $COCH_3$ | $CH=CH_2$ |
| 36 | $CO(CH_2)_3N(CH_3)_2$ | H | $COCH_3$ | $CH=CH_2$ |
| 37 | $CO(CH_2)_5NH_2$ | H | $COCH_3$ | $CH=CH_2$ |
| 38 | H | $CO(CH_2)_3NH_2$ | $COCH_3$ | $CH=CH_2$ |
| 39 | H | $COCH_2N\text{(piperidine)}$ | $COCH_3$ | $CH=CH_2$ |
| 40 | H | H | $CO(CH_2)_3N(CH_3)_2$ | $CH=CH_2$ |
| 41 | H | $CO(CH_2)_3N(CH_3)_2$ | $COCH_3$ | $CH_2CH_3$ |
| 42 | H | H | $COCH_2N(CH_3)_2$ | $CH_2CH_3$ |
| 43 | H | $COCH_2N(CH_3)_2$ | $COCH_3$ | $CH_2CH_3$ |
| 44 | H | $COCH_2N\text{(piperidine)}$ | $COCH_3$ | $CH_2CH_3$ |
| 45 | H | $CO(CH_2)_2N(CH_3)_2$ | $COCH_3$ | $CH_2CH_3$ |
| 46 | H | $COCH_2N(CH_3)_2$ | $COCH_3$ | cyclopropyl |
| 47 | H | H | $COCH_2N(CH_3)_2$ | cyclopropyl |
| 48 | H | $CO(CH_2)_2NHCH_3$ | $COCH_3$ | $CH=CH_2$ |
| 49 | H | $CO(CH_2)_2NH_2$ | $COCH_3$ | $CH=CH_2$ |
| 50 | H | $CO(CH_2)_2N\text{(pyrrolidine)}$ | $COCH_3$ | $CH=CH_2$ |

TABLE 1-continued

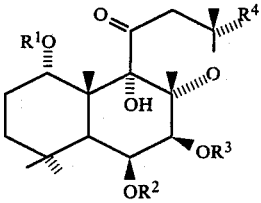

| No. | R¹ | R² | R³ | R⁴ |
|---|---|---|---|---|
| 51 | H | CO(CH₂)₂N⟨cyclohexyl⟩ | COCH₃ | CH=CH₂ |
| 52 | H | CO(CH₂)₂N⟨morpholino⟩ | COCH₃ | CH=CH₂ |

(Note: R² for 51 is CO(CH₂)₂N-piperidine; R² for 52 is CO(CH₂)₂N-morpholine)

Physiological activities of the present inventive compound are determined in the following ways:

1. Positive inotropic activity and hypotensive activity

Using adult dogs, either male or female, of the beagle or mixed breed as test animals, a polyethylene tube is inserted into the left ventricle of each animal through its carotid artery under anesthesia with pentobarbital sodium for the purpose of measuring the internal pressure of the left ventricle. Also a polyethylene tube is inserted into a femoral artery of the animal for the purpose of measuring blood pressure. Each polyethylene tube is connected to a pressure transducer and the pressure is recorded continuously on a recorder through a pressure strain gage. Further the rise rate of the left ventricle internal pressure (dp/dt) is determined by using a differential meter and recorded continuously in a similar way to serve as an index of the inotropic activity.

The activity of the test compounds is represented by the relative values to the maximum effects given by forskolin. The maximum increase in the rise rate (dp/dt) and the maximum decrease in the mean blood pressure (MBP), which are resulting from the intravenous administration of 30 μg/kg of forskolin, are assumed as 1, the activity of the test compounds is expressed as the relative values of those resulting from the intravenous administration of 300 μg/kg or 30 μg/kg of the test compounds.

2. Adenylate cyclase stimulating activity

A membrane fraction obtained from a homogenate of guinea pig myocardia was used as an authentic sample of adenylate cyclase [see G. I. Drummond, D. L. Severson, and L. Kuncan, J. Biol. Chem., 246, 4166 (1971)].

Labeled cAMP produced by adenylate cyclase from the labeled ATP as the substrate is determined according to the method of Salomon et al. [Y. Salomon, C. Londos, and M. Rodbell, Anal. Biochem., 58, 541 (1974)]. The reaction is initiated by adding the authentic enzyme to a solution of 25 mM Tris·HCl (pH 7.5) containing 5 mM of MgCl₂, 20 mM of creatine phosphate, 100 V/ml of creatine phosphokinase, 1 mM of cAMP, 1 mM of [¹⁴C (U)] ATP (ca. 7 cpm/pmol), and either forskolin or the test compound (1 μM), so that the final volume of the reaction mixture will become 100 μl. The authentic enzyme is used in an amount of 150 to 200 μg/100 μl as membrane protein. After 10 minute at 37° C., the reaction is stopped by adding 100 μl of a stop solution (pH 7.5) containing 2% of sodium dodecylsulfate (SDS), 40 mM of ATP, and 1.4 mM of cAMP, then 50 μl of [³H] cAMP (ca. 20,000 cpm) is added for the purpose of measuring the percentage of cAMP recovered. Thereafter, cAMP is isolated by chromatography on a Dowex 50 resin column and on a neutral alumina column and the radioactivity of the cAMP is determined.

The adenylate cyclase stimulating activity of the test compounds (1 μM) is expressed as the percentage of the activity based on that of forskolin (1 μM), [n=4 (n=6 for Nos. 10 and 17, n=2 for Nos. 38, 39, 41, 42), mean value ±standard deviation].

Table 2 shows results of the assays 1 and 2 on typical compounds of the present invention.

TABLE 2

Physiological actions of forskolin derivatives

| | | 1. Positive inotropic and hypotensive actions | | 2. Adenylate |
|---|---|---|---|---|
| Compound No. | Dose (μg/kg, i.v.) | Positive inotropic activity (dp/dt) | Hypotensive activity | cyclase activating activity (%) |
| 1 | 300 | 1.0 | 1.4 | 36.6 ± 3.8 |
| 6 | 300 | 1.1 | 1.5 | 33.5 ± 4.3 |
| 7 | 300 | 0.8 | 1.3 | 38.0 ± 2.2 |
| 8 | 300 | 1.3 | 1.2 | 39.8 ± 4.0 |
| 9 | 300 | 1.0 | 1.0 | 21.7 ± 3.0 |
| 10 | 300 | 1.1 | 2.0 | 90.4 ± 4.7 |
| 11 | 300 | 0.8 | 1.2 | 45.1 ± 6.9 |
| 12 | 300 | 0.8 | 1.0 | 40.2 ± 7.1 |
| 13 | 300 | 0.9 | 0.7 | 19.5 ± 0.5 |
| 14 | 300 | 1.0 | 1.1 | 27.1 ± 2.5 |
| 17 | 30 | 1.2 | 0.8 | 107.4 ± 7.1 |
| 18 | 300 | 1.0 | 1.5 | 127.9 ± 16.2 |
| 19 | 300 | 1.0 | 1.3 | 27.0 ± 5.6 |
| 20 | 30 | 1.0 | 0.9 | 91.1 ± 14.6 |
| 21 | 300 | 0.7 | 1.4 | 41.7 ± 3.5 |
| 26 | 300 | 0.6 | 0.2 | 22.0 ± 2.8 |
| 27 | 30 | 0.8 | 0.4 | 74.8 ± 3.8 |
| 29 | 300 | 0.6 | 0.05 | — |
| 30 | 300 | 0.9 | 0.6 | 20.8 ± 0.9 |
| 31 | 300 | 0.9 | 0.8 | 13.7 ± 1.3 |
| 36 | 300 | 0.5 | 0.2 | 16.7 ± 2.4 |
| 38 | 30 | 0.9 | 0.7 | 214.9 |
| 39 | 30 | 0.6 | 0.6 | 57.8 |
| 41 | 30 | 0.5 | 0.6 | 114.7 |
| 42 | 300 | 0.5 | 1.0 | 22.8 |
| 46 | 300 | 0.8 | 0.8 | — |

TABLE 2-continued

Physiological actions of forskolin derivatives

| Compound No. | Dose (μg/kg, i.v.) | 1. Positive inotropic and hypotensive actions | | 2. Adenylate cyclase activating activity (%) |
| --- | --- | --- | --- | --- |
| | | Positive inotropic activity (dp/dt) | Hypotensive activity | |
| 47 | 300 | 1.3 | 0.3 | — |

3. Solubility

As a result of measuring the solubility of the present inventive compound in water, all the compounds showed higher solubilities than forskolin.

Thus, the compounds of the present invention have excellent positive inotropic, hypotensive, and adenylate cyclase stimulating actions and higher water-solubility than those of forskolin. Therefore the present inventive compounds are expected to be effective as a remedy for chronic cardiac failure, hypotensive agent, and cerebral vasodilator, and in addition as a remedy for diseases, such as glaucoma, asthma, immunity failure, tumor, and digestive system diseases, which are caused by abnormal regulation of cAMP. Suitable doses of the compound for treating these diseases are generally from 0.01 to 30 mg/kg day though dependent on the disease state and age of the patient to be treated and on the way of administration.

Preferred compounds of the present invention are 6-dimethylaminoacetylforskolin (compound No. 10), 6-(3-dimethylaminopropionyl)forskolin (compound No. 17), 6-(4-dimethylaminobutyryl)forskolin (compound No. 20), 7-deacetyl-7-(2,3-dihydroxypropionyl)forskolin (compound No. 27), 6-(4-aminobutyryl)forskolin (compound No. 38), 6-pyrrolidinoacetyl)forskolin (compound No. 39), and 6-(4-dimethylaminobutyryl)-14,15-dihydroforskolin (compound No. 41). Among these compounds, compound Nos. 17, 20 and 38 are particularly superior in therapeutic efficacy and in other properties.

The present inventive compounds may be mixed with any suitable, pharmaceutically acceptable carrier to form tablets, granules, finer granules, powders, capsules, injectable compositions, suppositories, eye drops, plasters, ointments, and other forms of pharmaceutical compositions, which are administered orally or parenterally. The present compounds, are more water-soluble than forskolin, so they can be made up into drugs in the form of aqueous solution suitable for infusion or intravenous administration. Hence great therapeutic effects of the compounds are expected in the case of parenteral administration thereof.

The present invention is illustrated in more detail with reference to the following examples. However, these examples are not to be construed to limit the scope of the invention.

EXAMPLE 1

7-Deacetyl-7-dimethylaminoacetylforskolin (compound No. 1)

A solution (1 ml) of chloroacetyl chloride (250 mg) in dichloromethane is added to a mixture of 7-deacetylforskolin (500 mg), pyridine (250 mg), and dichloromethane (10 ml) under cooling with ice and stirred at room temperature for 1 hr. Further a solution (1 ml) of pyridine (75 mg) and acetyl chloride (75 mg) in dichloromethane is added under cooling with ice and the mixture is stirred at room temperature for 3 hr to complete the reaction. Then, the product solution is evaporated in vacuo to remove the dichloromethane and unreacted reagents, giving 7-deacetyl-7-chloroacetylforskolin in oily form, which is subjected to the next reaction without purification. That is, the oily product is dissolved in dichloromethane (10 ml), dimethylamine (3 ml) is added under cooling with ice, and the mixture is stirred for 1 hr to complete the reaction. This product solution is concentrated in vacuo, and after addition of water, the mixture is extracted with ethylacetate. The organic layer (extract solution) is washed with water, dried over magnesium sulfate, and filtered to remove the drying agent. The filtrate is concentrated in vacuo, and the concentrate (780 mg) is purified by chromatography on silica gel. The elusion with ethyl acetate yields 7-deacetyl-7-dimethylaminoacetylforskolin (468 mg, 76% yield based on 7-deacetyl-forskolin).

mp 162°–166° C. (recrystallized from hexane-ethyl acetate).

IR (nujol) ν: 3450, 3200, 1735, 1705 cm$^{-1}$.

MS m/z (relative intensity): 453 (M$^+$, 5), 357 (6), 102 (71), 59 (52), 58 (100).

This crystalline product is dissolved in dioxane, and an equimolar amount of HCl dissolved in dioxane is added to give hydrochloride of the product.

mp 284°–287° C. (EtOH).

IR (nujol) ν: 1740, 1710 cm$^{-1}$.

Compound Nos. 2–6 are also obtained according to the above procedure but using amines shown in the following table in place of dimethylamine.

In the table;

Yields are based on 7-deacetylforskolin.

IR (nujol) ν: cm$^{-1}$.

MS: m/z (relative intensity).

TABLE 3

| Compound No. | Amine | Yield | mp | IR | MS |
| --- | --- | --- | --- | --- | --- |
| 2 | n-BuNH$_2$ | 14% | 175–178° C. (hexane-ethyl acetate) | 3610 3520 3320 1730 1710 | 481 (M$^+$, 10) 385 (5) 350 (5) 324 (7) 132 (100) 86 (100) |
| 3 | Et$_2$NH | 90% | 130–135° C. (hexane-ethyl acetate) | 3300 3180 1740 1710 | 481 (M$^+$, 12) 385 (3) 130 (72) 88 (100) 87 (100) 58 (61) |
| 4 | Pyrrolidine | 71% | 178–182° C. (hexane-ethyl acetate) | 3500 3440 3160 1750 1710 | 479 (M$^+$, 1) 130 (6) 128 (9) 85 (7) 84 (100) |
| 5 | Piperazine | 32% | Oily matter | — | 494 (M$^+$, 3) 452 (2) 382 (10) 145 (28) 99 (100) |
| 6 | Morpholine | 28% | 182–185° C. (hexane-ethyl acetate) | 3490 3140 1755 1715 | 495 (M$^+$, 2) 399 (2) 146 (9) 144 (10) 100 (100) |

EXAMPLE 2

7-Deacetyl-7-(3-dimethylaminopropionyl)forskolin (compound No. 7)

A mixture of forskolin (15 g), t-butyldimethylchlorosilane (11.25 g), imidazole (5.25 g), and N,N-dimethylformamide (45 ml) is stirred at 70° C. for 21 hr to complete the reaction. Then, the product solution is poured into water and this mixture is extracted with ethyl acetate. The organic layer is washed with water, dried over magnesium sulfate, and filtered to remove the drying agent. The filtrate is concentrated in vacuo to give crude 1-(t-butyldimethylsilyl)forskolin (21.62 g).

This oily product (21.62 g) is dissolved in methanol (250 ml), and 1N aqueous NaOH (40 ml) is added dropwise to the solution under cooling with ice. This reaction mixture is stirred at room temperature overnight to complete the reaction, and then concentrated in vacuo. The concentrate, after addition of water, is extracted with ethyl acetate. The organic layer is washed with water, dried over magnesium sulfate, and filtered to remove the drying agent. The filtrate is concentrated in vacuo and the concentrate (20 g) is purified by chromatography on silica gel. The elusion with hexane-ethyl acetate (5:1) yields 1-(t-butyldimethylsilyl)-7-deacetylforskolin (17.42 g, 99% yield based on forskolin) in oily form.

IR (neat) $\nu$: 3500, 3300, 1710 cm$^{-1}$.

MS m/z (relative intensity): 482 (M$^+$, 0.8), 466 (100), 407 (8), 311 (20), 191 (36), 75 (100).

3-chloropropionyl chloride (513 mg) is added dropwise to a mixture of the oily product (1.5 g), pyridine (320 mg), and dichloromethane (10 ml). After 5 hr stirring at room temperature, pyridine (320 mg) and 3-chloropropyionyl chloride (513 mg) are added to the mixture. This reaction mixture is stirred at room temperature overnight to complete the reaction. The product solution, after addition of water, is extracted with ethyl acetate. The organic layer is washed with water, dried, and filtered to remove the used drying agent. The filtrate is concentrated to give crude 1-(t-butyldimethylsilyl)-7-(3-chloropropionyl)-7-deacetylforskolin (2.09 g) in oily form.

To a solution (10 ml) of this oily product (1 g) in dichloromethane is added an excess of dimethylamine under cooling with ice. This mixture is stirred at room temperature for 2 hr to complete the reaction. Then, the product solution is concentrated to give crude 1-(t-butyldimethylsilyl)-7-deacetyl-7-(3-dimethylaminopropionyl)forskolin (877 mg) in oily form.

$^1$H-NMR (CDCl$_3$)$\delta$: 5.44 (1H, d, J=4.6 Hz), 4.62 (1H, br s), 4.60 (1H, br s), 2.86 (6H, s), 1.70 (3H, s), 1.45 (3H, s), 1.33 (3H, s), 1.26 (3H, s), 1.05 (3H, s), 0.87 (9H, s), 0.14 (3H, s), 0.02 (3H, s).

To a methanolic solution (10 ml) of this oily product (865 mg) is added trifluoroacetic acid (4 ml) under cooling with ice. The mixture is stirred at room temperature for 43 hr to complete the reaction, and then concentrated. This concentrate is diluted with dil. hydrochloric acid, and washed with ethyl acetate. The separated aqueous layer is made alkaline with 28% aqueous ammonia and extracted with ethyl acetate. The organic layer is washed with water, dried over magnesium sulfate, and filtered to remove the drying agent. The filtrate is concentrated and subjected to recrystallization from hexane-dichloromethane, yielding 7-deacetyl-7-(3-dimethylaminopropionyl)forskolin (283 mg) [yield: 41% based on 1-(t-butyldimethylsilyl)-7-deacetylforskolin].

mp 150°–153° C.

MS m/z (relative intensity): 467 (M$^+$, 2), 202 (2), 159 (8), 118 (29), 92 (61), 91 (81), 58 (100).

Using diethylamine in place of dimethylamine, compound No. 25 is obtained in the form of colorless oil.

Yield: 69.1%.

MS m/Z: 495 (M+).

EXAMPLE 3

7-Deacetyl-7-(4-pyrrolidinobutyryl)forskolin (compound No. 8)

A solution (10 ml) of 4-chlorobutyryl chloride (800 mg) in dichloromethane is added to a mixture of 7-deacetylforskolin (1.3 g), pyridine (700 mg), and dichloromethane (40 ml) under cooling with ice. This reaction mixture is stirred at room temperature for 3 hr to complete the reaction. The product solution is concentrated in vacuo, and purified by chromatography on silica gel. The elution with hexane-ethyl acetate yields 7-(4-chlorobutyryl)-7-deacetylforskolin (1.27 g) in oily form.

$^1$H-NMR (CDCl$_3$) $\delta$: 5.53 (1H, d, J=5 Hz), 4.58 (1H, br s), 4.48 (1H, br s), 3.64 (2H, t, J=6 Hz), 2.62 (2H, m), 2.18 (4H, m), 1.73 (3H, s), 1.45 (3H, s), 1.35 (3H, s), 1.27 (3H, s), 1.04 (3H, s).

A mixture of this oily product (1.27 g), pyrrolidine (20 ml), and dichloromethane (50 ml) is stirred at room temperature for 5 days to complete the reaction. The product solution is concentrated in vacuo, and after addition of water, is extracted with ethyl acetate. The organic layer is washed with water, dried over magnesium sulfate, and filtered to remove the drying agent. The filtrate is concentrated in vacuo and then purified by chromatography on silica gel. The elution with chloroform-methanol yields 7-deacetyl-7-(4-pyrrolidinobutyryl)forskolin (109 mg, 6% yield based on 7-deacetylforskolin).

$^1$H-NMR (CDCl$_3$) $\delta$: 5.37 (1H, d, J=4 Hz), 4.56 (1H, m), 4.50 (1H, m), 2.53 (8H, m), 1.93 (2H, m), 1.79 (4H, m), 1.73 (3H, s), 1.44 (3H, s), 1.35 (3H, s), 1.26 (3H, s), 1.03 (3H, s), MS m/z (relative intensity): 507 (M$^+$, 4), 199 (3), 156 (26), 140 (10), 92 (40), 91 (52), 84 (100).

EXAMPLE 4

6-Dimethylaminoacetyl-7-deacetylforskolin (compound No. 9)

7-Deacetyl-7-dimethylaminoacetylforskolin (200 mg) of Example 1 is dissolved in an acetonitrile-water (45:55) mixture (20 ml), 1N aqueous NaOH (0.8 ml) is added, and the solution is stirred at room temperature for 25 min to complete the reaction. The product solution is concentrated in vacuo, and after addition of water, is extracted with ethyl acetate. The organic layer is washed with water, dried over magnesium sulfate, and filtered to remove the drying agent. The filtrate is concentrated in vacuo and the concentrate (242 mg) is purified by chromatography on silica gel. The elution with acetonitrile yields 6-dimethylaminoacetyl-7-deacetylforskolin (176 mg, 88% yield).

mp 116°–117° C. (hexane-ethylacetate).

IR (nujol) $\nu$: 3410, 3200, 1750, 1720 cm$^{-1}$.

MS m/z: 453 (m$^+$, 5), 350 (2), 237 (2), 219 (2), 104 (15), 58 (100).

This crystalline product is dissolved in dioxane and an equimolar amount of HCl dissolved in dioxane is added to yield hydrochloride of the product.

mp 263°–265° C. (EtOH).

IR (nujol) ν: 3490, 3230, 2680, 1745, 1710 cm$^{-1}$.

The following compounds are obtained by the same rearrangement reaction using the corresponding 7-substituted 7-deacetyl forskolins.

with hexane-ether (1:3) yields 6-dimethylaminoacetyl-forskolin (444 mg, 69% yield).

mp 190°–193° C. (toluene).

IR (nujol) ν: 3100, 1750, 1730, 1720 cm$^{-1}$.

$^1$H-NMR (CDCl$_3$) δ: 5.86 (1H, q, J=4 Hz, J=2.7 Hz), 5.56 (1H, d, J=4.9 Hz), 4.61 (1H, br s), 3.18 (2H, s), 2.31 (6H, s), 2.04 (3H, s), 1.64 (3H, s), 1.42 (3H, s), 1.35 (3H, s), 1.04 (3H, s), 0.96 (3H, s).

TABLE 4

| Compound No. | Yield | mp | $^1$H-NMR (CDCl$_3$) δ | MS |
|---|---|---|---|---|
| 14 | 83% | 84–86° C. (hexane-ethyl acetate) | 5.89 (1H, q, J=4Hz, J=2.7 Hz)<br>4.66 (1h, br s)<br>429 (1H, d, J=4 Hz)<br>3.34 (2H, center of AB quartet, J=17.3 Hz)<br>2.71 (4H, q, J=7 Hz)<br>1.62 (3H, s)<br>1.42 (3H, s)<br>1.40 (3H, s)<br>1.08 (3H, s)<br>1.06 (3H, t, J=7 Hz)<br>0.98 (3H, s) | 481 (M$^+$, 5)<br>130 (13)<br>87 (25)<br>86 (100) |
| 16 | 30% | — | 5.94 (1H, q, J=4.8 Hz, J=1 Hz)<br>4.66 (1H, br s)<br>4.31 (1H, d, J=4.3 Hz)<br>3.43 (2H, center of AB quartet, J=17.3 Hz)<br>2.63 (2H, t, J=Hz)<br>1.59 (3H, s)<br>1.49 (2H, m)<br>1.42 (3H, s)<br>1.39 (3H, s)<br>1.35 (2H, m)<br>1.08 (3H, s)<br>0.98 (3H, s)<br>0.91 (3H, t, J=7.3 Hz) | 481 (M$^+$, 2)<br>463 (0.8)<br>132 (35)<br>86 (100) |
| 19 | 38% | 159–162° C. | 5.90 (1H, t, J=6.7 Hz)<br>4.65 (1H, br s)<br>4.26 (1H, d, J=4 Hz)<br>2.33 (4H, m)<br>2.20 (6H, s)<br>1.78 (2H, m)<br>1.62 (3H, s)<br>1.42 (3H, s)<br>1.41 (3H, s)<br>1.07 (3H, s)<br>0.97 (3H, s) | 481 (M$^+$, 12)<br>173 (13)<br>132 (100)<br>114 (50)<br>91 (19) |
| 23 | 87.1% | Colorless oily matter | — | 467 (M$^+$) |
| 24 | 33.9% | Colorless oily matter | — | 495 (M$^+$) |

EXAMPLE 5

6-Dimethylaminoacetylforskolin (compound No. 10)

A mixture of pyridine (1 g) and acetyl chloride (750 mg) is added in 4 parts to a mixture of 6-dimethylaminoacetyl-7-deacetylforskolin (compound No. 9, 587 mg) and dichloromethane (20 ml) and stirred at room temperature for 7 hr to complete the reaction. The product solution, after addition of water, is made alkaline with a saturated aqueous sodium hydrogencarbonate (NaHCO$_3$) solution, and extracted with dichloromethane. The organic layer is dried over magnesium sulfate, and filtered to remove the drying agent. The filtrate is concentrated, and the concentrate (811 mg) is purified by chromatography on silica gel. The elution Hydrochloride of this product is obtained in the same manner as in Example 4.

mp 255°–260° C. (EtOH).

IR (nujol) ν: 3240, 3130, 2400, 1750, 1725 cm$^{-1}$.

Compound Nos. 11 and 12 are produced according to the procedure of this example but using propionyl chloride and butyryl chloride, respectively, in place of acetyl chloride.

Also, compound Nos. 15, 17, 18 and 20 are produced according to the procedure of this example but using 6-diethylaminoacetyl-7-deacetylforskolin (compound No. 14), 6-(3-dimethylaminopropionyl)-7-deacetylforskolin (compound No. 23), 6-(3-diethylaminopropionyl)-7-deacetylforskolin (compound No. 24), and 6-(4-dimethylaminobutyryl)-7-deacetylforskolin (compound No. 19), respectively, in place of 6-dimethylaminoacetyl-7deacetylforskolin.

TABLE 5

| Compound No. | Yield | mp | $^1$H-NMR (CDCl$_3$) | MS |
|---|---|---|---|---|
| 11 | 39% | | 5.86 (1H, q, J=4.5 Hz, J=3.1 Hz) | 509 (M$^+$, 35) |

TABLE 5-continued

| Compound No. | Yield | mp | ¹H-NMR (CDCl₃) | MS |
|---|---|---|---|---|
| | | | 5.57 (1H, d, J=4.4 Hz) | 219 (26) |
| | | | 4.60 (1H, br s) | 160 (57) |
| | | | 3.16 (2H, s) | 104 (100) |
| | | | 2.37 (6H, s) | 102 (100) |
| | | | 2.31 (1H, q, J=7.5 Hz) | |
| | | | 2.30 (1H, q J=7.5 Hz) | |
| | | | 1.64 (3H, s) | |
| | | | 1.42 (3H, s) | |
| | | | 1.34 (3H, s) | |
| | | | 1.15 (3H, t, J=7.5 Hz) | |
| | | | 1.04 (3H, s) | |
| | | | 0.96 (3H, s) | |
| 12 | 38% | | 5.81 (1h, q, J=4.3 Hz, J=2.7 Hz) | |
| | | | 5.58 (1H, d, J=4.7 Hz) | |
| | | | 4.60 (1H, br s) | |
| | | | 3.16 (2H, s) | |
| | | | 2.37 (6H, s) | |
| | | | 2.27 (1H, t, J=7.4 Hz) | |
| | | | 2.26 (1H, t, J=7.4 Hz) | |
| | | | 1.66 (2H, m) | |
| | | | 1.65 (3H, s) | |
| | | | 1.42 (3H, s) | |
| | | | 1.33 (3H, s) | |
| | | | 1.04 (3H, s) | |
| | | | 0.96 (3H, s) | |
| | | | 0.95 (3H, t, J=7.4 Hz) | |
| 15 | 46% | | 5.84 (1H, q, J=4.0 Hz, J=2.7 Hz) | 523 (M⁺,1) |
| | | | 5.55 (1H, d, J=4.3 Hz) | 508 (0.5) |
| | | | 4.61 (1H, br s) | 316 (2) |
| | | | 3.33 (2H, s) | 132 (26) |
| | | | 2.70 (4H, q, J=6.9 Hz) | 130 (17) |
| | | | 2.02 (3H, s) | 95 (11) |
| | | | 1.66 (3H, s) | 87 (42) |
| | | | 1.43 (3H, s) | 86 (100) |
| | | | 1.35 (3H, s) | |
| | | | 1.07 (6H, t, J=6.9 Hz) | |
| | | | 1.03 (3H, s) | |
| | | | 0.96 (3H, s) | |
| 17 | 32% | 176–177° C. (diethyl ether) | 5.54 (1H, q, J=4.3 Hz, J=2.7 Hz) | 509 (M⁺, 3) |
| | | | 5.52 (1H, d, J=4 Hz) | 186 (2) |
| | | | 4.62 (1H, br s) | 160 (4) |
| | | | 2.46–2.73 (5H, m) | 118 (17) |
| | | | 2.25 (6H, s) | 92 (25) |
| | | | 2.02 (3H, s) | 91 (38) |
| | | | 1.66 (3H, s) | 58 (100) |
| | | | 1.44 (3H, s) | |
| | | | 1.35 (3H, s) | |
| | | | 1.03 (3H, s) | |
| | | | 0.97 (3H, s) | |
| 18 | 34% | — | 5.84 (1H, q, J=4.3 Hz, J=2.7 Hz) | — |
| | | | 5.52 (1H, d, J=4.4 Hz) | |
| | | | 4.61 (1H, br s) | |
| | | | 2.85 (2H, m) | |
| | | | 2.51 (6H, m) | |
| | | | 2.02 (3H, s) | |
| | | | 1.66 (3H, s) | |
| | | | 1.44 (3H, s) | |
| | | | 1.35 (3H, s) | |
| | | | 1.04 (6H, t, J=7.1 Hz) | |
| | | | 1.03 (3H, s) | |
| | | | 0.97 (3H, s) | |
| 20 | 31% | 238–240° C. (tetrahydrofuran-methanol) | 584 (1H, q, J=4 Hz, J=3 Hz) | 523 (M⁺, 5) |
| | | | 5.52 (1H, d, J=4 Hz) | 174 (4) |
| | | | 4.61 (1H, br s) | 132 (20) |
| | | | 2.35 (4H, m) | 114 (23) |
| | | | 2.22 (6H, s) | 92 (11) |
| | | | 2.02 (3H, s) | 91 (17) |
| | | | 1.81 (2H, m) | 58 (100) |
| | | | 1.65 (3H, s) | |
| | | | 1.43 (3H, s) | |
| | | | 1.35 (3H, s) | |
| | | | 1.03 (3H, s) | |
| | | | 0.97 (3H, s) | |

EXAMPLE 6

6-Dimethylaminoacetyl-7-deacetyl-7-dimethylaminoacetylforskolin (compound No. 13)

Chloroacetyl chloride (209 mg) is added dropwise to a mixture of 6-dimethylaminoacetyl-7-deacetylforskoline (compound No. 9, 700 mg), pyridine (146 mg), and dichloromethane (10 ml) under cooling with ice. This reaction mixture is stirred for 3 hr while cooling with ice to complete the reaction, and then concentrated. The concentrate, diluted with water, is made alkaline with a saturated aqueous NaHCO$_3$ solution, and extracted with ethyl acetate. The organic layer is washed with water, dried over magnesium sulfate, and filtered to remove the drying agent. The filtrate is concentrated to give 7-chloroacetyl-7-deacetyl-6-dimethylaminoacetylforskolin (749 mg) in the form of white solid.

A solution (20 ml) of this white solid (749 mg) in dichloromethane is added dropwise to a solution (20 ml) of excess dimethylamine in dichloromethane under cooling with ice and stirred at room temperature for 1 hr to complete the reaction. The product solution, after addition of water, is extracted with dichloromethane. The organic layer is dried over magnesium sulfate and then filtered to remove the drying agent. The filter is concentrated, and the concentrate (728 mg) is purified by chromatography on silica gel. The elution with dichloromethane-acetone (2:1) yields 6-dimethylaminoacetyl-7-deacetyl-7-dimethylaminoacetylforskolin (186 mg, 23% yield based on compound No. 9).

mp 180°–183° C. (hexane-ethyl acetate).

MS m/z (relative intensity): 538 (M+, 58), 454 (8), 104 (100), 102 (100).

According to the above procedure, 6-acetyl-7-deacetylforskolin is converted into 6-acetyl-7-chloroacetyl-7-deacetylforskolin, which in turn is reacted with dimethylamine, thereby yielding 6-acetyl-7-deacetyl-7-dimethylaminoacetylforskolin (compound No. 21, 88% yield base on 6-acetyl-7-deacetylforskolin).

$^1$H-NMR (CDCl$_3$) δ: 5.82 (1H, q, J=4.7 Hz, J=3.0 Hz), 5.62 (1H, d, J=4.4 Hz), 4.61 (1H, br s), 3.15 (2H, center of AB quartet, J=17 Hz), 2.37 (6H, s), 2.09 (3H, s), 1.66 (3H, s), 1.44 (3H, s), 1.33 (3H, s), 1.03 (3H, s), 0.98 (3H, s).

In the same manner, 6-acetyl-7-deacetylforskolin is converted into 6-acetyl-7-(4-chlorobutyryl)-7-deacetylforskolin by using 4-chlorobutyryl chloride.

$^1$H-NMR (CDCl$_3$) δ: 5.83 (1H, q, J=4.3 Hz, J=3.1 Hz), 5.55 (1H, d, J=4.6 Hz), 4.63 (1H, br s), 3.52 (2H, m), 2.38–2.6 (4H, m), 2.10 (3H, s), 2.04–2.2 (3H, m), 1.67 (3H, s), 1.44 (3H, s), 1.36 (3H, s), 1.04 (3H, s), 0.98 (3H, s).

This product compound is reacted with pyrrolidine to yield 6-acetyl-7-deacetyl-7-(4-pyrrodinobutyryl)-forskolin (compound No. 22, 14% yield based on 6-acetyl-7-deacetylforskolin).

$^1$H-NMR (CDCl$_3$) δ: 5.81 (1H, q, J=4.3 Hz, J=2.9 Hz), 5.54 (1H, d, J=4.6 Hz), 4.60 (1H, br s), 2.62 (6H, m), 2.28–2.44 (3H, m), 2.09 (3H, s), 1.75–1.95 (6H, m), 1.65 (3H), 1.44 (3H, s), 1.35 (3H, s), 1.03 (3H, s), 0.98 (3H, s).

EXAMPLE 7

7-Deacetyl-7-hemiglutarylforskolin (compound No. 26)

A mixture of 7-deacetylforskolin (369 mg), glutaric anhydride (342 mg), and pyridine (5 ml) is heated at 110° C. for 2 hr to complete the reaction. The product solution is concentrated in vacuo, and after addition of water, is extracted with ethyl acetate. The organic layer is washed with an aqueous copper sulfate solution, dried over magnesium sulfate, and filtered to remove the drying agent. The filtrate is concentrated in vacuo, and purified by chromatography on silica gel. The adsorbate is eluted successively with hexane-acetic acid (2:1) and chloroform-methanol (9:1), yielding 7-deacetyl-7-hemiglutarylforskolin (compound No. 26, 270 mg, 56% yield) in oily form.

$^1$H-NMR (CDCl$_3$) δ: 5.49 (1H, d, J=4.0 Hz), 4.58(1H, br s), 4.47 (1H, t, J=3.7 Hz), 2.50 (4H, m), 2.20 (2H, m), 2.05 (2H, m), 1.73 (3H, s), 1.45 (3H, s), 1.35 (3H, s), 1.27 (3H, s), 1.04 (3H, s).

MS m/z (relative intensity): 482 (M+, 7), 464 (62), 436 (10), 227 (41), 115 (84), 81 (100).

EXAMPLE 8

7-Deacetyl-7-(2,3-dihydroxypropionyl)forskolin (compound No. 27)

A solution (4 ml) of 2,2-dimethyl-1,3-dioxolane-4-carboxylic chloride (360 mg) in dichloromethane is added dropwise to a mixture of 7-deacetylforskolin (500 mg), pyridine (300 mg), and dichloromethane (10 ml) under cooling with ice. This reaction mixture is stirred at room temperature for 4 hr to complete the reaction. The product solution is concentrated in vacuo, and the concentrate (950 mg) is purified by chromatography on silica gel. The elution with dichloromethane-ethyl acetate (10:1) yield mixed diastereomers of 7-deacetylforskolin-7-(2,2-dimethyl-1,3-dioxolane-4-carboxylate) (557 mg, 83% yield).

mp 160°–165° C.

MS m/z (relative intensity): 496 (M+, 2), 478 (40), 131 (32), 123 (36), 101 (100), 59 (30).

This 7-deacetylforskolin-7-(2,2-dimethyl-1,3-dioxolane-4-carboxylate) (300 mg) and 70% acetic acid (10 ml) are mixed and stirred at 60° C. for 2 hr to complete the reaction. The product solution is concentrated in vacuo, and the concentrate (470 mg) is purified by chromatography on silica gel. The elution with dichloromethane-ethyl acetate (2:1) yields mixed diastereomers (A:B=3:2) of 7-deacetyl-7-(2,3-dihydroxypropionyl)-forskolin (250 mg, 91% yield).

mp 160°–172° C.

IR (nujol) ν: 3440, 3320, 1750, 1730, 1700 cm$^{-1}$

MS m/z (relative intensity): 456 (M+, 5), 438 (77), 123 (94), 99 (80), 81 (100).

EXAMPLE 9

6-Hemisuccinylforskolin (compound No. 29)

(1) A mixture of forskolin (1 g), t-butyldimethylsilyl chloride (1.2 g), imidazole (1.25 g), and N,N-dimethylformamide (2 ml) is left standing at 60° C. for 2 hr. The product solution is poured into ice water, and the mixture is extracted with ether. The ether layer is washed with water, dried over anhydrous sodium sulfate, and filtered to remove the drying agent. The filterate is concentrated in vacuo to yield 1-(t-butyldimethylsilyl)-forskolin (1.2 g) in the form of colorless oil.

(2) The obtained oily matter (1.2 g) is dissolved in methanol (10 ml), 1N aqueous NaOH is added to the solution, and this reaction mixture is stirred at room temperature for 3 hr to complete the reaction. The product solution is diluted with water and extracted with ethyl acetate. The organic layer is washed with water, dried over anhydrous sodium sulfate, and filtered to remove the drying agent. The filtrate is concentrated in vacuo, and the concentrate (1.0 g) is purified by chromatography on silica gel. The elution with hexane-ethyl acetate (5:1) yields 1-(t-butyldimethylsilyl)-7-deacetylforskolin (0.85 g) in the form of colorless oil.

(3) After 1-(t-butyldimethylsilyl)-7-deacetylforskolin (0.44 g) has been dissolved in pyridine (2.0 ml), succinic anhydride (4 g) is added and the mixture is heated under reflux for 2 hr to complete the reaction. The pyridine is removed from the product solution by evaporation in vacuo, and the residue is thoroughly washed with ethyl acetate and 0.1N aqueous HCl to extract the product in the ethyl acetate. The organic layer is washed with water, dried over anhydrous sodium sulfate, and filtered to remove the drying agent. The filtrate is concentrated in vacuo to yield 1-(t-butyldimethylsilyl)-7-hemisuccinyl-7-deacetylforskolin (0.53 g, yield: quantitative) in oily form.

(4) This oily matter (250 mg) is dissolved in an acetonitrile-water (1:1) mixture (10 ml) and 1N aqueous NaOH (1 ml) is added to the solution. This reaction mixture is stirred at room temperature for 30 min to complete the reaction. The product solution, diluted with water, is adjusted with 0.5N aqueous HCl to pH 3 and then extracted with ethyl acetate. The organic layer is washed with water, dried over anhydrous sodium sulfate, and filtered to remove the drying agent. The filtrate is concentrated, and purified by chromatography on silica gel, yielding 1-(t-butyldimethylsilyl)-6-hemisuccinyl-7-deacetylforsklin (178 mg, 71.2% yield) in the form of colorless oil.

(5) This oily matter (178 mg) is dissolved in pyridine (0.4 ml) and acetic anhydride (0.4 ml) is added to the solution under cooling with ice. This reaction mixture is allowed to stand overnight at 4° C. The product solution is poured into ice-water and the mixture is extracted with ethyl acetate. The organic layer is washed with water, dried over anhydrous sodium sulfate, and filtered to remove the drying agent, and the filtrate is concentrated in vacuo. The resulting crude product is purified by chromatography on silica gel, yielding 1-(t-butyldimethylsilyl)-6-hemisuccinylforskolin (183 mg, 96.3% yield) in the form of colorless oil.

(6) This oily matter (75 mg) is dissolved in methanol (1 ml) and trifluoroacetic acid (1.5 ml) is added to the solution. This reaction mixture is stirred at room temperature for 4 hr. The product solution is neutralized by adding a saturated aqueous $NaHCO_3$ solution and then extracted with ethyl acetate. The organic layer is washed with water, dried over anhydrous sodium sulfate, and filtered to remove the drying agent. The filtrate is concentrated in vacuo to yield 6-hemisuccinyl-forskolin (compound No. 29, 32 mg, 52.2% yield) in the form of colorless oil.

NMR ($CDCl_3$) δ: 1.01, 1.38, 1.42, 1.61, 1.69, 2.01 (each, 3H, s, Me), 2.01 (3H, s, OAc), 2.60–2.80 (4H, m, —$COCH_2CH_2CO$—), 4.61 (1H, br s, 1β-H), 4.98 (1H, d, J=8 Hz, 15-H), 5.28 (1H, d, J=17.5 Hz, 15-H), 5.52 (1H, d, J=3 Hz, 7α-H), 5.83 (1H, t, 3.5 Hz, 6α-H), 5.97 (1H, dd, J=8, J=17.5 Hz, 14-H).

EXAMPLE 10

6-Hemisuccinyl-7-deacetylforskolin (compound No. 28)

1-(t-Butyldimethylsilyl)-6-hemisuccinyl-7-deacetylforskolin (260 mg) of Example 9-(4) is treated according to the procedure of Example 9-(6) to remove the protecting substituent, i.e. 1-(t-butyldimethylsilyl group, thereby yielding 6-hemisuccinyl-7-deacetylforskolin (compound No. 28, 140 mg, 67% yield) in the form of colorless oil.

MS m/z (relative intensity): 468 ($M^+$).

EXAMPLE 11

Forskolin-1-hemisuccinate (compound No. 31)

A mixture of forskolin (1 g), succinic anhydride (4.9 g), 4-morpholino-N,N'-dicyclohexylcarbodiimide (1.1 g), and pyridine (8 ml) is heated at 100° C. for 1 hr to complete the reaction. The product solution is concentrated in vacuo, and after addition of 0.5N aqueous HCl, is extracted with ethyl acetate. The ethyl acetate layer is washed with a saturated aqueous NaCl solution, dried over anhydrous sodium sulfate, and filtered to remove the drying agent. The filtrate is concentrated in vacuo and purified by chromatography on silica gel. The elution with chloroform-methanol (96:4) and then with chloroform-methanol-acetic acid (18:2:0.5) yields forskolin-1-hemisuccinate (compound No. 31, 0.7 g) in the form of colorless oil.

$^1$H—NMR (sodium salt, $CDCl_3$) δ: 5.50 (1H, d, J=4 Hz), 5.50 (1H, s), 4.46 (1H, br s), 2.50–2.30 (4H, m), 2.16 (3H, s), 1.67 (3H, s), 1.51 (3H, s), 1.31 (3H, s), 1.25 (3H, s), 1.02 (3H, s).

MS (EI, 70 eV, methyl ester derivative) m/z (relative intensity): 506 ($[M-18]^+$, 5), 243 (7), 191 (33), 151 (31), 115 (100), 107 (45).

Forskolin-1-hemisuccinate in the form of sodium salt is obtained by dissolving the acid form in a 5% aqueous $NaHCO_3$ solution, adsorbing the acid on Amberlite XAD-II, washing it with water, and eluting the adsorbate with methanol.

Forskolin-1-hemiglutarate (compound No. 32) can be produced according to the above procedure but using glutaric anhydride in place of succinic anhydride.

$^1$H—NMR (sodium salt, $CDCl_3$) δ: 5.57 (1H, br s), 5.48 (1H, d, J=4 Hz), 4.55 (1H, t, J=3.7 Hz), 2.5–2.2 (4H, m), 2.0–1.8 (2H, m), 2.18 (3H, s), 1.71 (3H, s), 1.54 (3H, s), 1.34 (3H, s), 1.28 (3H, s), 1.05 (3H, s).

MS (EI, 70 eV, methyl ester derivative) m/z (relative intensity): 520 ($[M-18]^+$, 30), 259 (7), 219 (5), 191 (3), 175 (6), 129 (100).

EXAMPLE 12

Forskolin-1-hemiadipate (compound No. 33)

Pyridine (0.2 ml) is added to a solution (10 ml) of forskolin (0.12 g) and adipic dichloride (0.5 g) in dichloromethane under cooling with ice. This reaction mixture is stirred at room temperature for 4 hr. The product solution is poured into a 5% aqueous $NaHCO_3$ solution under cooling with ice to decompose the acid chloride. Then the pH of the solution is adjusted to 3 with 0.5N aqueous HCl. To this solution is added ethyl acetate to extract the product. The organic layer is washed with a saturated aqueous NaCl solution, dried over anhydrous sodium sulfate, concentrated in vacuo, and purified by chromatography on a thin layer of silica gel. The adsorbate is eluted with chloroform-methanol-acetic acid (9:1:0.1) and fractions of pH values between 0.3 and 0.5 are collected, therefrom yielding forskolin-1-hemiadipate (compound No. 33, 0.065 g) in the form of colorless oil.

$^1$H—NMR (sodium salt, $CDCl_3$) δ: 5.56 (1H, br s), 5.51 (1H, d, J=4 Hz), 4.46 (1H, t, J=3.2 Hz), 2.5–2.0

(4H, m), 1.8–1.5 (4H, m), 2.18 (3H, s), 1.70(3H, s), 1.53 (3H, s), 1.33 (3H, s), 1.24 (3H, s), 1.05 (3H, s).

MS (EI, 70 eV, methyl ester derivative) m/z (relative intensity): 5.34 ([M-18]+, 68), 282 (7), 259 (14), 219 (13), 191 (61), 143 (100).

The above product is then transformed into its sodium salt in the same manner as in the case of compound No. 31.

Forskolin-1-hemioxalate (compound No. 30) can be produced according to the above procedure.

MS (FAB) m/z: 483 (M+H), 591 (MH+108).

EXAMPLE 13

Forskolin-1-(4-dimethylaminobutyrate) (compound No. 36)

A mixture of forskolin (0.20 g), N,N-dimethylaminobutyric acid hydrochloride (0.25 g), dicyclohexylcarbodiimide (0.40 g), 4-dimethylaminopyridine (0.30 g), and dichloromethane (5 ml) is subjected to reaction at room temperature for 2 hr. The precipitated crystals are filtered, and the filtrate is made alkaline with a 5% aqueous NaHCO solution and extracted with ethyl acetate. The organic layer is washed with water, dried over anhydrous sodium sulfate, and filtered to remove the drying agent. The filtrate is concentrated in vacuo and purified by chromatography on silica gel. The elution with ethyl acetate and then with ethyl acetate-methanol-triethylamine (95:5:1) yields forskolin-1-(4-dimethylaminobutyrate) (compound No. 36, 0.19 g) in the form of colorless oil.

$^1$H—NMR (CDCl$_3$) δ: 5.55 (1H, s), 5.53 (1H, d, J=4.8 Hz), 4.47 (1H, br s), 2.5–2.1 (4H, m), 2.18 (6H, s), 2.17 (3H, s), 1.71 (3H, s), 1.85–1.65 (2H, m), 1.54 (3H, s), 1.35 (3H, s), 1.28 (3H, s), 1.06 (3H, s).

MS (FAB) m/z (relative intensity): 524 (M+H, 100), 632 (MH+ 108, 78).

EXAMPLE 14

Forskolin-1-glycinate (compound No. 34) (1) A mixture of forskolin (0.3 g), N-t-butoxycarbonylglycine (0.3 g), dicyclohexylcarbodiimide (0.4 g), 4-dimethylaminopyridine (0.3 g), and dichloromethane (5 ml) is stirred at room temperature for 2 hr. The precipitated crystals is separated from the product solution by filtration, and the filtrate is extracted with ethyl acetate. The organic layer is washed with water, dried over anhydrous sodium sulfate, and filtered to remove the drying agent. The filtrate is concentrated in vacuo and chromatographed on a silica gel column. The elution with ethyl acetate-benzene (5:95) and then with ethyl acetate-benzene (10:90) yields forskolin-1-N-BOC-glycinate (0.31 g) in the form of colorless oil.

$^1$H—NMR (CDCl$_3$) δ: 5.61 (1H, br s), 5.42 (1H, d, J=4 Hz), 4.45 (1H, s), 3.80 (2H, d, J=5.3 Hz), 2.17 (3H, s), 1.74 (3H, s), 1.55 (3H, s), 1.45 (9H, s), 1.34 (3H, s), 1.29 (3H, s), 1.05 (3H, s).

(2) Then, this forskolin-1-N-BOC-glycinate (0.31 g) is dissolved in acetic acid (0.5 ml), and a hydrobromic acid-acetic acid solution (0.5 ml) is added under cooling with ice. This reaction mixture is left standing at room temperature for 10 min. The excess hydrochloric acid in the product solution is neutralized with a 5% aqueous NaHCO$_3$ solution. The resulting solution is chromatographed on an Amberlite XAD-2 resin column, the column is washed with water, and the adsorbate is eluted with methanol, yielding forskolin-1-glycinate (compound 34, 0.12 g) in the form of colorless oil.

MS (FAB) m/z (relative intensity): 468 (MH), 576 (MH+108).

In the same way as above, forskolin-1-(6-aminocaproate) (compound No. 37) and forskolin-1-(4-aminobutyrate) (compound No. 35) can be produced.

Forskolin-1-(6-aminocaproate) (compound 37): Oily matter

MS (FAB) m/z: 524 (M+ H), 632 (MH+108).

Forskolin-1-(4-aminobutyrate) (compound No. 35): Oily matter

MS (FAB) m/z: 496 (M+ H), 604 (MH+108).

EXAMPLE 15

6-(4-Aminobutyryl)forskolin (compound No. 38) (1) A mixture of
4-(t-butoxycarbonylamino)butyric acid (8.20 g),
4-dimethylaminopyridine (6.40 g), and
dicyclohexylcarbodiimide (12.60 g) is added in 4 parts to a mixture of 7-deacetylforskolin (3.00 g) and dichloromethane (100 ml) under cooling with ice. This reaction mixture is stirred overnight at room temperature to complete the reaction. The product solution, after addition of water (0.5 ml), is concentrated in vacuo. Dichloromethane is added to the concentrate and the insoluble matter is removed therefrom by filtration. The filtrate is concentrated and purified by chromatography on a silica gel column. The elution with dichloromethane-ethyl acetate (10:1) yields 7-[4-(t-butoxycarbonylamino)butyryl]-7-deacetylforskolin (compound No. 38a, 1.60 g, 36% yield) in the form of colorless oil.

MS m/z (relative intensity): 535 ([M-H$_2$O]+, 23), 479 (23), 104 (34), 86 (81), 57 (100).

(2) To a mixture of this oily product (compound No. 38a, 1.50 g), acetonitrile (90 ml), and water (60 ml) is added 1-N aqueous NaOH (6 ml), and the mixture is stirred at room temperature for 40 min. Immediately after completion of the reaction, the product solution is concentrated, and after addition of water, is extracted with ethyl acetate. The extract solution is dried over magnesium sulfate, and filtered to remove the drying agent. The filtrate is concentrated and the concentrate (1.43 g) is purified by chromatography on a silica gel column. The elution with dichloromethane-ethyl acetate (4:1-2:1) yield 6-[4-(t-butoxycarbonylamino)-butyryl]-7deacetylforskolin (compound No. 38b, 1.12 g, 75% yield).

mp 188°–190° C. (ethyl acetate).

IR (nujor) ν: 3350, 1735, 1710 cm$^{-1}$.

(3) This compound (No. 38b, 1.12 g) is dissolved in dichloromethane (80 ml), and a mixture of pyridine (1.52 g) and acetyl chloride (675 mg) is added in 3 parts to the solution. This reaction mixture is stirred at room temperature for 8 hr and then water is added to end the reaction. The product solution is extracted with dichloromethane, and the organic layer is dried over magnesium sulfate, and filtered to remove the drying agent. The filtrate is concentrated, and the concentrate (1.97 g) is purified by chromatography on a silica gel column. The elution with dichloromethane-ethyl acetate (10:1-5:1) yields 6-[4-(t-butoxycarbonylamino]butyryl)-forskolin (compound No. 38c, 414 mg, 34% yield);

mp 162°–165° C. (hexane-toluene).

(4) This compound (No. 38c, 123 mg) is dissolved in 85% formic acid under cooling with ice to react therewith. This solution is stirred at room temperature for 2 hr to complete the reaction. The product solution is concentrated, diluted with water, and washed with ethyl acetate. The aqueous layer is made alkaline with 3N aqueous $Na_2CO_3$ and extracted with ethyl acetate. The organic layer is dried over magnesium sulfate and filtered to remove the drying agent. The filtrate is concentrated and subjected to recrystallization from ethyl acetatemethanol, yielding 6-(4-aminobutyryl)forskolin (compound No. 38, 31 mg, 30% yield).

mp 191°–192° C.

IR (nujol) $v$: 3360, 1725 $cm^{-1}$.

$^1H$—NMR ($CD_3OD$) δ: 5.76 (1H, q, J=4.7 Hz, J=3.3 Hz), 5.39 (1H, d, J=4.3 Hz), 4.42 (1H, br s), 2.59 (2H, t, J=6.0 Hz), 2.2–2.4 (2H, m), 1.88 (3H, s), 1.8–1.6 (3H, m), 1.56 (3H, s), 1.37 (3H, s), 1.23 (3H, s), 0.91 (6H, s).

MS m/z (relative intensity): 495 (M , 14), 146 (32), 104 (100), 99 (13), 86 (74).

The following compounds are obtained in the same way as in Example 15 by using the corresponding starting materials.

No. 48 6-(3-Methylaminopropionyl) forskolin hydrochoride.

Form Colorless powdery crystal (ethanol).

mp 245°–246° C. (dec).

IR (KBr)$v$: 1710, 1740, 3200 $cm^{-1}$.

$^1H$—NMR ($CDCl_3$)δ: 5.86 (1H, g, J=45 Hz, J=2.9 Hz), 5.55 (1H, d, J=45 Hz), 4.60 (1H, br, s), 2.46–3 (6H, m), 2.45 (3H, s), 2.03 (3H, s), 1.64 (3H, s), 1.43 (3H, s), 1.35 (3H, s), 1.03 (3H, s), 0.97 (3H, s).

MS (FAB) m/z (relative intensity): 496 (M+H, 46%), 104 (100%).

No. 49 6-(3-Aminopropionyl) forskolin hydrochloride.

Form Colorless powdery crystal (ethanol).

mp 270°–271° C. (dec).

IR (NBr): 1715, 1730, 3200 $cm^{-1}$.

$^1H$—NMR ($CDCl_3$): 5.87 (1H, g, J=4.5 Hz, J=3.0 Hz), 5.56 (1H, d, J=4.5 Hz), 4.60 (1H, br, s), 2.4–3.1 (6H, m), 2.03 (s, 3H), 1.65 (s, 3H), 1.43 (s, 3H), 1.35 (s, 3H), 1.03 (s, 3H), 0.97 (s, 3H).

MS (FAB) mz (relative intensity): 482 (M+H, 100%)

EXAMPLE 16

6-Pyrrolidinoacetylforskolin (compound No. 39)

(1) 7-Deacetyl-7-pyrrolidinoacetylforskolin (4.20 g), which is obtainable in the same way as in Example 15-(1) but using pyrrolidinoacetic acid in place of 4-(t-butoxycarbonylamino)butyric acid, is dissolved in an acetonitrile-water (4:1) mixture (150 ml), and 1-N aqueous NaOH (9.63 ml) is added dropwise to the solution under cooling with ice. This reaction mixture is stirred at room temperature for 6 hr and then water is added to end the reaction. The product solution is extracted with ethyl acetate, and the organic layer is concentrated and dissolved in ether. The ether solution is extracted with 1-N aqueous HCl. Aqueous ammonia is added dropwise to the aqueous layer of extract solution under cooling with ice to make the solution alkaline, and this solution is extracted with ether. The organic layer is dried over magnesium sulfate and then filtered to remove the drying agent. The filtrate is concentrated, and purified by chromatography on a silica gel column. The elution with dichloromethanemethanol (20:1) yields 7-deacetyl-6-pyrrolidinoacetyl-forskolin (compound No. 39a, 900 mg, 21% yield).

IR (KBr) $v$: 3460, 3210, 1745, 1710 $cm^{-1}$.

MS m/z (relative intensity): 479 (M+, 1), 130 (8), 84 (100).

(2) Pyridine (72 mg) and acetyl chloride (72 mg) are added each in 4 times over 6 hr to a mixture of the above obtained compound (No. 39a, 100 mg) and dichloromethane (10 ml) under cooling with ice. This reaction mixture is stirred overnight at room temperature and then extracted with dichloromethane. The organic layer is washed with a saturated aqueous NaCl solution, dried over magnesium sulfate, and filtered to remove the drying agent. The filtrate is concentrated and the concentrate (120 mg) is purified by chromatography on a silica gel column. The elution with chloroform-methanol (20:1) yields 6-pyrrolidinoacetylforskolin (compound No. 39, 53 mg, 50% yield).

mp 166°–168° C. (dichloromathane-hexane).

IR (KBr) $v$: 3450, 3230, 1750, 1715 $cm^{-1}$.

The following compounds are obtained in the same way as in Example 16 by using the corresponding starting materials.

No. 50 6-(3-Pyrrolidinopropionyl) forskolin hydrochloride.

No. 51 6-(3-Piperidinopropionyl) forskolin hydrochloride.

No. 52 6-(3-Morpholinopropionyl) forskolin hydrochloride.

EXAMPLE 17

7-Deacetyl-7-(4-dimethylaminobutyryl)forskolin (compound No. 40)

A mixture of dicyclohexylcarbodiimide (35.82 mg) and dichloromethane (120 ml) is added dropwise to a mixture of 7-deacetylforskoline (8.00 g), 4-dimethylaminobutyric acid hydrochloride (14.56 g), 4-dimethylaminopyridine (21.21 g), and dichloromethane (150 ml) under cooling with ice. This reaction mixture is stirred at room temperature for 4 hr to complete the reaction. The product solution is extracted with dil. aqueous HCl. The aqueous layer, made alkaline with conc. aqueous ammonia, is extracted with diethyl ether. The organic layer is washed with water, dried over anhydrous magnesium sulfate, and filtered to remove the drying agent. The filtrate is concentrated in vacuo, yielding 7-deacetyl-7-(4-dimethylaminobutyryl)forskolin (5.41 g, 52% yield based on 7-deacetylforskolin) in oily form.

MS m/z: 481 (M+).

EXAMPLE 18

6-(4-Dimethylaminobutyryl)-14,15-dihydroforskolin (compound No. 41)

A mixture of 6-(4-dimethylaminobutyryl)forskolin (30 mg), a 5% palladium-on-carbon catalyst (6 mg), and methanol (8 mg) is stirred under a hydrogen atmosphere at room temperature for 5 hr to complete the reaction. The product solution is filtered to remove the catalyst. The filtrate is concentrated to yield 6-(4-dimethylaminobutyryl)-14,15-dihydroforskolin (compound No. 41, 30 mg, 100% yield).

mp 210°–212° C. (methanol)

IR (nujol) $v$: 3160, 1730, 1740 $cm^{-1}$.

Compound Nos. 42–45, as shown in Table 6, are produced in the same way as in this example.

NMR and MS of compound Nos. 41, 43 and 45 are as shown in Table 7.

TABLE 6

| Compound | | | | Starting |
|---|---|---|---|---|
| No. | Name | Properties | Yield | material |
| 42 | 14,15-Dihydro-7-deacetyl-7-dimethylaminoacetyl-forskolin | m.p. 187–188° C. (ethyl acetate) IR (nujol) $v$: 3470, 3180, 1750, 1700 cm$^{-1}$ | 100% | 7-Deacetyl-7-dimethylamino-acetylforskolin |
| 43 | 6-Dimethylaminoacetyl-14,15-dihydroforskolin | Apperance: white solid MS m/z: 497 (M$^+$) | 100% | 6-Dimethyl-aminoacetyl-forskolin |
| 44 | 6-Pyrrolidinoacetyl-14,15-dihydroforskolin | Appearance: white solid MS m/z: 507 (M$^+$) | 100% | Compound No. 39 |
| 45 | 6-(3-Dimethylamino-propionyl)-14,15-dihydroforskolin | Appearance: white solid Ms m/z: 511 (M$^+$) | 100% | 6-(3-Dimethyl-aminopropionyl)-forskolin |

TABLE 7

| Compound No. | $^1$H-NMR | MS (m/z) (rel. intensity) |
|---|---|---|
| 41 | (Solvent, DMSO-d$_6$) $\delta$: 5.64 (1H, t, J=4.0 Hz) 5.34 (1H, d, J=4.0 Hz) 4.34 (1H, br s) 2.4–2.3 (2H, m) 2.28 (2H, t, J=7.0 Hz) 2.09 (6H, s) 1.91 (3H, s) 1.8–1.6 (2H, m) 1.6–1.4 (2H, m) 1.49 (3H, s) 1.37 (3H, s) 1.15 (3H, s) 0.92 (3H, s) 0.91 (3H, s) 0.81 (3H, t, J=6.8 Hz) | 525 (M$^+$ 26) 200 (6) 174 (10) 132 (64) 114 (52) 58 (100) |
| 43 | (Solvent, CD$_3$OD) $\delta$: 5.9–5.8 (1H, m) 5.49 (1H, t, J=5.5 Hz) 4.41 (1H, br s) 1.99 (3H, s) 1.98 (6H, s) 1.58 (3H, s) 1.47 (3H, s) 1.22 (3H, s) 1.01 (3H, s) 1.00 (3H, s) 0.89 (3H, t, J=7.3Hz) | 497 (M$^+$) |
| 45 | (Solvent, CDCl$_3$) $\delta$: 5.83 (1H, q, J=4.3 Hz, 3.1 Hz) 5.49 (1H, d, J=4.4 Hz) 4.55 (1H, br s) 2.73 (2H, m) 2.57 (2H, m) 2.32 (6H, s) 2.01 (3H, s) 1.58 (3H, s) 1.46 (3H, s) 1.24 (3H, s) 1.02 (3H, s) 0.97 (3H, s) 0.90 (3H, t, J=7 Hz) | 511 (M$^+$, 7) 160 (7) 118 (39) 116 (10) 58 (100) |

The starting material for producing compound No. 42 can be prepared according to the procedure of Example 17 but using N,N-dimethylglcine hydrochloride in place of 4-dimethylaminobutyric acid hydrochloride.

The starting materials for producing compound Nos. 43, 44 and 45 can be prepared according to the procedure of Example 15 but using N,N-dimethylglycine hydrochloride, pyrrolidinoacetic acid, and 3-dimethylaminopropionic acid, respectively, in place of 4-(t-butoxycarbonylamino)butyric acid.

EXAMPLE 19

13-Cyclopropyl-6-dimethylaminoacetyl-14,15-dinorforskolin (compound No. 46)

An ethereal solution of diazomethane is added to a mixture of 6-dimethylaminoacetylforskolin (100 mg), palladium acetate (14 mg), and anhydrous tetrahydrofuran (5ml) under cooling with ice. This reaction mixture is stirred for 3 hr still under cooling with ice to complete the reaction. Water is added to the product solution, and the mixture is adjusted to pH 10 with a 3N aqueous Na$_2$CO$_3$ solution and extracted with ethyl acetate. The organic layer is dried over magnesium sulfate, and filtered to remove the drying agent. The filtrate is concentrated, and purified by chromatography on a silica gel column. The elution with dichloromethane-ether (4:1-2:1) yields 13-cyclopropyl-6-dimethylaminoacetyl-14,15-dinorforskolin (compound No. 46, 16 mg, 16% yield).

IR (nujol) $v$: 3570, 3180, 1735, 1715 cm$^{-1}$.

$^1$H—NMR (CDCl$_3$) $\delta$: 0.30 (2H, m), 0.41 (1H, m), 0.75 (1H, m), 0.91 (1H, m), 0.95 (3H, s), 1.03 (3H, s), 1.32 (3H, s), 1.44 (3H, s), 1.54 (3H, s), 2.01 (3H, s), 2.43 (6H, s), 3.23 (2H, s), 4.51 (1H, br s), 5.51 (1H, d, J=5 Hz), 5.83 (1H, t, J=4 Hz).

MS m/z (relative intensity): 510 (M$^+$, 23), 109 (49), 04 (100), 81 (49), 59 (100), 58 (100).

According to the above procedure, 13-cyclopropyl-deacetyl-7-dimethylaminoacetyl-14,15-dinorforskolin compound No. 4, 60% yield) is produced from 7-deacetyl-7dimethylaminoacetylforskolin.

IR (nujol) $v$: 3250, 1740, 1705 cm$^{-1}$.

$^1$H—NMR (CDCl$_3$) $\delta$: 0.18 (2H, m), 0.49 (1H, m), 0.89 (1H, m), 0.96 (1H, m), 1.01 (3H, s), 1.28 (3H, s), 1.30 (3H, s), 1.50 (3H, s), 1.66 (3H, s), 2.38 (6H, s), 3.27 (2H, s), 4.43 (1H, br s), 4.47 (1H, br s), 5.43 (1H, d, J=4.5 Hz).

MS m/z (relative intensity): 467 (M$^+$, 4), 109 (26), 104 (58), 102 (60), 85 (41), 58 (100).

EXAMPLE 20

7-Deacetyl-7-(3-dimethylaminopropionyl)forskolin (compound No. 7)

A mixture of 4-dimethylaminopyridine (3.00 g), 3-dimethylaminopropionic acid hydrochloride (3.80 g), and dicyclohexylcarbodiimide (7.00 g) is added in 3 parts over 47 hr to a solution (60 ml) of 7-deacetylforskoline (2.00 g) in dichloromethane. This reaction mixture is stirred at room temperature. After completion of the reaction, the solvent is evaporated in vacuo from the product solution. The resulting residue is dissolved in ethyl acetate, and the solution is filtered. The filtrate is concentrated, and the concentrate (6.05 g) is purified by chromatography on silica gel. The elution with dichloromethane-methanol (20:1-10:1) yields 7-deacetyl-7-(3-dimethylaminopropionyl)forskolin (compound No. 7, 1.72 g, 68% yield).

What is claimed is:

1. A forskolin derivative represented by the formula

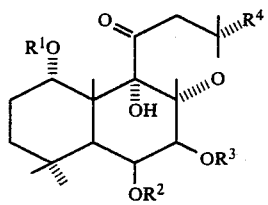

wherein;

$R^1$ is hydrogen and $R^4$ is vinyl, ethyl, or cyclopropyl, and (1) either of $R^2$ and $R^3$ denotes a residue represented by the formula

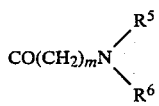

wherein each of $R^5$ and $R^6$ denotes hydrogen or lower alkyl and m is an integer of 1 to 5, and the other one of $R^2$ and $R^3$ denotes hydrogen or a residue represented by the formula $CO(CH_2)_nX$, X being hydrogen or

wherein, each of $R^7$ and $R^8$ denotes hydrogen or lower alkyl and n being an integer of 1 to 5, or (2) $R^2$ denotes hydrogen or $-COCH_2CH_2CO_2H$ and $R^3$ denotes hydrogen, $-COCH_3$, $-COCH_2CH_2CH_2CO_2H$, or $-COCH(OH)CH_2OH$ with the proviso that $R^3$ is one of the last two residues when $R^2$ is hydrogen, and physiologically acceptable salts of said forskolin derivative.

2. The forskolin derivative and its physiologically acceptable salt according to claim 1, wherein $R^2$ in the formula is H or

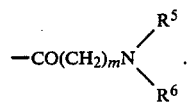

3. The forskolin derivative and its physiologically acceptable salt according to claim 1, where, in the formula, (A) $R^1$ is H, $R^2$ is

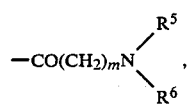

$R^3$ is $-CO(CH_2)_nX$, and $R^4$ is $-CH=CH_2$ or $-CH_2CH_3$ or (B) $R^1$ is H, $R^3$ is $-COCH(OH)CH_2(OH)$, and $R^4$ is $-CH=CH_2$.

4. The forskolin derivative and its physiologically acceptable salt according to claim 1, where, in the formula, $R^1$ is H, $R^2$ is $-COCH_2N(CH_3)_2$, $-CO(CH_2)_2N(CH_3)_2$, $-CO(CH_2)_3N(CH_3)_2$, or $-CO(CH_2)_3NH_2$, and $R^3$ is $-COCH_3$.

5. 6-[3-(Dimethylamino)propionyl]forskolin and its physiologically acceptable salt.

6. 6-[4-(dimethylamino)butyryl]forskolin and its physiologically acceptable salt.

7. 6-(4-Aminobutyryl)forskolin and its physiologically acceptable salt.

8. The forskolin derivative and its physiologically acceptable salt according to the claim 4, wherein $R^2$ is $-CO(CH_2)_2N(CH_3)_2$.

* * * * *